United States Patent
Calhoun et al.

(10) Patent No.: US 10,143,585 B2
(45) Date of Patent: Dec. 4, 2018

(54) SYSTEMS AND METHODS FOR TREATING EYE DISEASES USING RETROGRADE BLOOD FLOW

(71) Applicant: J.D. Franco & Co., Plano, TX (US)

(72) Inventors: Michael Calhoun, Lighthouse Point, FL (US); Jeff Franco, Plano, TX (US); Robert M. Vidlund, Forest Lake, MN (US)

(73) Assignee: J.D. Franco & Co., LLC, Plano, TX (US)

( * ) Notice: Subject to any disclaimer, the term of this patent is extended or adjusted under 35 U.S.C. 154(b) by 0 days.

(21) Appl. No.: 15/971,680

(22) Filed: May 4, 2018

(65) Prior Publication Data
US 2018/0250161 A1    Sep. 6, 2018

Related U.S. Application Data

(63) Continuation of application No. 15/681,075, filed on Aug. 18, 2017, now Pat. No. 9,987,164, which is a
(Continued)

(51) Int. Cl.
*A61F 9/007* (2006.01)
*A61F 2/966* (2013.01)
(Continued)

(52) U.S. Cl.
CPC ............. *A61F 9/007* (2013.01); *A61F 2/856* (2013.01); *A61F 2/966* (2013.01); *A61F 9/00781* (2013.01); *A61F 2002/821* (2013.01)

(58) Field of Classification Search
CPC ...... A61F 2/856; A61F 9/00781; A61F 9/007; A61F 2/966; A61F 2002/821
See application file for complete search history.

(56) References Cited

U.S. PATENT DOCUMENTS 2,690,595 A   10/1954   Raiche
3,367,101 A   2/1968    Garnet et al.
(Continued)

FOREIGN PATENT DOCUMENTS

WO   WO 98/52639 A1   11/1998
WO   WO 98/53761 A1   12/1998
(Continued)

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.
(Continued)

*Primary Examiner* — Julian W Woo
(74) *Attorney, Agent, or Firm* — Bookoff McAndrews, PLLC

(57) ABSTRACT

A method, device, or system for treating eye disorders or conditions, comprising restoring or increasing blood flow or blood flow rate in an artery that supplies blood to or in the eye, thereby increasing the amount of nutrient(s) that reaches the eye or a portion thereof. The invention also includes methods, devices, or systems for treating eye disorders or conditions which use reverse flow or retrograde flow structures and systems during the treatment of the eye disease.

30 Claims, 2 Drawing Sheets

Related U.S. Application Data continuation of application No. PCT/US2017/021673, filed on Mar. 9, 2017.

(60) Provisional application No. 62/396,091, filed on Sep. 16, 2016, provisional application No. 62/314,340, filed on Mar. 28, 2016, provisional application No. 62/305,991, filed on Mar. 9, 2016.

(51) Int. Cl.
*A61F 2/856* (2013.01)
*A61F 2/82* (2013.01)

(56) References Cited

U.S. PATENT DOCUMENTS

| | | | |
|---|---|---|---|
| 3,435,826 | A | 4/1969 | Fogarty |
| 4,403,612 | A | 9/1983 | Fogarty |
| 4,926,858 | A | 5/1990 | Gifford, III et al. |
| 5,026,384 | A | 6/1991 | Farr et al. |
| 5,176,693 | A | 1/1993 | Pannek, Jr. |
| 5,395,311 | A | 3/1995 | Andrews |
| 5,709,701 | A | 1/1998 | Parodi |
| 5,820,595 | A | 10/1998 | Parodi |
| 5,897,567 | A | 4/1999 | Ressemann et al. |
| 6,146,370 | A | 11/2000 | Barbut |
| 6,206,868 | B1 | 3/2001 | Parodi |
| 6,302,908 | B1 | 10/2001 | Parodi |
| 6,336,933 | B1 | 1/2002 | Parodi |
| 6,344,054 | B1 | 2/2002 | Parodi |
| 6,413,235 | B1 | 7/2002 | Parodi |
| 6,423,032 | B2 | 7/2002 | Parodi |
| 6,540,712 | B1 | 4/2003 | Parodi et al. |
| 6,623,471 | B1 | 9/2003 | Barbut |
| 6,641,573 | B1 | 11/2003 | Parodi |
| 6,645,222 | B1 | 11/2003 | Parodi et al. |
| 6,824,558 | B2 | 11/2004 | Parodi |
| 6,827,726 | B2 | 12/2004 | Parodi |
| 6,837,881 | B1 | 1/2005 | Barbut |
| 6,855,162 | B2 | 2/2005 | Parodi |
| 6,902,540 | B2 | 6/2005 | Dorros et al. |
| 6,905,490 | B2 | 6/2005 | Parodi |
| 6,908,474 | B2 | 6/2005 | Hogendijk et al. |
| 6,929,634 | B2 | 8/2005 | Dorros et al. |
| 6,936,053 | B1 | 8/2005 | Weiss |
| 6,936,060 | B2 | 8/2005 | Hogendijk et al. |
| 7,214,201 | B2 | 5/2007 | Burmeister et al. |
| 7,235,095 | B2 | 6/2007 | Haverkost et al. |
| 7,309,334 | B2 | 12/2007 | Von Hoffmann |
| 7,604,612 | B2 | 10/2009 | Ressemann et al. |
| 7,867,273 | B2 | 1/2011 | Pappas et al. |
| 7,901,445 | B2 | 3/2011 | Walker et al. |
| 7,927,347 | B2 | 4/2011 | Hogendijk et al. |
| 8,157,760 | B2 | 4/2012 | Criado et al. |
| 8,353,850 | B2 | 1/2013 | Ressemann et al. |
| 8,414,516 | B2 * | 4/2013 | Chang ............. A61B 17/12136 604/8 |
| 8,545,432 | B2 | 10/2013 | Renati et al. |
| 8,834,404 | B2 | 9/2014 | Beaudin |
| 8,852,226 | B2 | 10/2014 | Gilson et al. |
| 8,863,631 | B1 | 10/2014 | Janardhan et al. |
| 9,078,682 | B2 | 7/2015 | Lenker et al. |
| 9,241,699 | B1 | 1/2016 | Kume et al. |
| 9,259,215 | B2 | 2/2016 | Chou et al. |
| 9,265,512 | B2 | 2/2016 | Garrison et al. |
| 2001/0001114 | A1 | 5/2001 | Tsugita et al. |
| 2002/0087128 | A1 | 7/2002 | Paques et al. |
| 2002/0151922 | A1 | 10/2002 | Hogendijk et al. |
| 2003/0023200 | A1 | 1/2003 | Barbut et al. |
| 2003/0023227 | A1 | 1/2003 | Zadno-Azizi et al. |
| 2003/0199802 | A1 | 10/2003 | Barbut |
| 2003/0199819 | A1 | 10/2003 | Beck |
| 2003/0203958 | A1 | 10/2003 | Kunz et al. |
| 2005/0149117 | A1 | 7/2005 | Khosravi et al. |
| 2006/0136022 | A1 | 6/2006 | Wong, Jr. et al. |
| 2006/0259132 | A1 | 11/2006 | Schaffer et al. |
| 2008/0027519 | A1 | 1/2008 | Guerrero |
| 2008/0243229 | A1 | 10/2008 | Wallace et al. |
| 2009/0018455 | A1 | 1/2009 | Chang |
| 2009/0024072 | A1 | 1/2009 | Criado et al. |
| 2009/0030323 | A1 | 1/2009 | Fawzi et al. |
| 2010/0125244 | A1 | 5/2010 | McAndrew |
| 2011/0143993 | A1 | 6/2011 | Langer et al. |
| 2011/0152683 | A1 | 6/2011 | Gerrans et al. |
| 2011/0160762 | A1 | 6/2011 | Hogendijk et al. |
| 2012/0046679 | A1 | 2/2012 | Patel et al. |
| 2012/0078287 | A1 | 3/2012 | Barbut |
| 2012/0101510 | A1 | 4/2012 | Lenker et al. |
| 2013/0197621 | A1 | 8/2013 | Ryan et al. |
| 2013/0281788 | A1 | 10/2013 | Garrison |
| 2014/0154246 | A1 | 6/2014 | Robinson et al. |
| 2015/0313607 | A1 | 11/2015 | Zhadkevich |
| 2015/0366580 | A1 | 12/2015 | Lenihan et al. |
| 2016/0166754 | A1 | 6/2016 | Kassab et al. |

FOREIGN PATENT DOCUMENTS

| | | |
|---|---|---|
| WO | WO 00/54673 A1 | 9/2000 |
| WO | WO 03/018085 A2 | 3/2003 |
| WO | WO 2007/103464 A2 | 9/2007 |
| WO | WO 2014/022866 A1 | 2/2014 |
| WO | WO 2016/109586 A1 | 7/2016 |

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

Yamane, T. et al., "The technique of ophthalmic arterial infusion therapy for patients with intraocular retinoblastoma," International Journal of Clinical Oncology, Apr. 2004; vol. 9, Issue 2, pp. 69-73.

(56) References Cited

OTHER PUBLICATIONS

Zeumer, H. et al., "Local intra-arterial fibrinolytic therapy in patients with stroke: urokinase versus recombinant tissue plagminogen activator (r-TPA)," Neuroradiology, 1993; 35: pp. 159-162.
Zipfel, P.F., et al., "The Role of Complement in AMD," Inflammation and Retinal Disease: Complement Biology and Pathology, Advances in Experimental Medicine and Biology, 2010, 703, pp. 9-24.
Examination Report No. 2 for AU Application No. 2013296195, dated Jun. 27, 2017 (6 pages).
Notice of Allowance for KR 20157005602, dated Sep. 25, 2017 (3 pages).
Loh, K. et al., "Prevention and management of vision loss relating to facial filler injections." Singapore Medical Journal, 2016; 57(8): 438-443.
International Search Report and Written Opinion for International Application No. PCT/US2017/0051551, dated Dec. 15, 2017 (14 pages).
International Search Report and Written Opinion for International Application No. PCT/US2017/0052901, dated Dec. 8, 2017 (9 pages).

\* cited by examiner

SYSTEMS AND METHODS FOR TREATING EYE DISEASES USING RETROGRADE BLOOD FLOW

CROSS-REFERENCE TO RELATED APPLICATIONS

This application is a continuation of U.S. application Ser. No. 15/681,075, filed Aug. 18, 2017, now U.S. Pat. No. 9,987,164, which is a continuation application of International Application No. PCT/US2017/021673, filed on Mar. 9, 2017, which claims the benefit of priority of U.S. Provisional Application No. 62/396,091, filed Sep. 16, 2016, U.S. Provisional Application No. 62/314,340, filed Mar. 28, 2016, and U.S. Provisional Application No. 62/305,991, filed Mar. 9, 2016, all of which are incorporated by reference herein in their entireties.

FIELD OF THE INVENTION

The present invention relates to treating eye diseases and conditions.

BACKGROUND OF THE INVENTION

Diseases of the eye, specifically age-related macular degeneration (AMD), glaucoma and diabetic retinopathy affect a large percentage of the population. In part, most of the diseases of the eye are treated by treating one or more symptoms, but failing to address the underlying cause(s) of the disease or condition. These therapies are therefore deficient in one or more aspects, necessitating improved approaches.

In a general sense, the pathogenesis of some of these eye diseases is similar if not the same as those seen for cardiac diseases and for abdominal aorta conditions. However, the anatomy of the vasculature behind the eye is typically smaller, includes more branches, and includes more sharp angles in the blood flow pathway. Further, the vascular system supplying blood to the eye is closer to the brain; any uncaptured or non-rerouted debris may cause an immediate stroke.

The use of catheter delivery systems for positioning and deploying therapeutic devices, such as balloons, stents and embolic devices, in the vasculature of the human body has become a standard procedure for treating endovascular diseases. It has been found that such devices are particularly useful as an alternative in treating areas where traditional operational procedures are impossible or pose a great risk to the patient. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

BRIEF SUMMARY OF THE INVENTION

In accordance with the present invention, diseases and conditions of the eye may be directly mediated by compromised blood flow to the vasculature of the eye. The present invention treats eye diseases by restoring blood flow using a reverse flow or retrograde flow device and system.

In a reverse flow embolic protection method, an arterial access cannula is connected to a venous cannula in order to establish a reverse or retrograde flow from an artery (such as the internal carotid artery and/or ophthalmic artery) through the arterial cannula and away from the eye and/or vasculature of the eye. Flow in an artery is occluded, typically by inflating a balloon on the distal tip of the cannula, in a carotid artery, the internal carotid artery (ICA), or the ophthalmic artery (OA), thereby reversing blood flow in the ICA and/or the OA. After such reverse or retrograde flow is established, any catheter or interventional procedure in the ophthalmic artery can be performed with a greatly reduced risk of emboli entering the eye.

The present invention is also directed to one or more intravascular medical devices and methods intended to sufficiently unblock or partially restore blood flow in a blocked or partially blocked artery such that nutrient(s) content is increased distal to the blockage. An embodiment of the invention is directed to devices and methods for restoring blood flow through the ostium. An embodiment of the invention includes using these devices and methods to restore or increase blood flow to the eye or a portion thereof. An embodiment of the invention includes restoring or increasing nutrient levels in the eye or a portion thereof. Restoring or increasing blood flow may include using these devices and methods, or equivalent devices and methods, but is not to be limited thereby.

The inventors believe that any blockage or reduction in fluid or blood flow is a mediator of certain consequences described more particularly below. As used herein, blockage refers to complete or partial blockage; reduced, restricted, or eliminated blood flow; sometimes caused by plaque, tortuous shaped anatomy, vessel failure or dysfunction.

While not intending to be restricted to any particular theory of operation, function, or causal connection, the inventors believe any condition, such as a blockage, that leads to lowered nutrient availability and/or consumption is a direct mediator of normal physiologic function. The inventors also believe that those conditions also mediate metabolic waste removal from cells, organs, and other biological structures.

Possible conditions include but are not limited to one or more of the following: reduced or blocked blood flow in one or more arteries or system of arteries; reduced or blocked source of energy or nutrients to a cell, organelle of a cell; mitochondrion; group of cells, or organ; altered aerobic energy metabolism; altered mitochondria oxidative phosphorylation; decreased or blocked supply of glucose; decreased hemoglobin amount or delivery to one or more intra-cranial structures or to one or more eye tissues; reduced blood flow or rate anywhere in the fluid flow path between the ICA and eye tissue; and any blockage or partial blockage in one or more arteries or system of arteries; any mediation of the complement system, the complement cascade, and/or one of the complement cascade associated molecules; and lowered/blocked nutrient supply and/or metabolic waste removal is implicated, and therefore may mediate one or more diseases, disorders, or biological function.

These conditions may occur in one or more of the following areas or structures: one or more arteries; one or more cranial arteries; and one or more arteries associated with of supplying blood flow to the eye; the internal carotid artery; the ophthalmic artery; anywhere in the fluid flow path between the ICA and eye tissue; the junction between the ICA and the OA, which is referred to in this disclosure as the ostium; and secondary areas of the anatomy include the vascular system commonly referred to as the terminal branches. These areas include, but are not limited to the Supra orbital Artery (SOA), the Supra Trochlear Artery (STA), the dorsal Nasal Artery (DNA), and the facial Arteries (FA); any cranial artery; and in any of the junctions or ostia between any of the vasculature between the ICA and one or more eye tissues.

Examples of diseases and conditions include, but are not limited to, any of a variety of eye diseases, including but not limited to AMD (both dry and wet); neuronal cell death; Alzheimer's disease; dementia; glaucoma; diabetic macula edema, macular telangiectasia (e.g., type 1 or 2 macular telangiectasia), atrophic macular degeneration, chorioretinopathy (e.g., central serous chorioretinopathy), retinal inflammatory vasculopathy, pathological retinal angiogenesis, age-related maculopathy, retinoblastoma, Pseudoxanthoma elasticum, a vitreoretinal disease, choroidal subretinal neovascularization, central serous chorioretinopathy, ischemic retinopathy, hypertensive retinopathy or diabetic retinopathy (e.g., nonproliferative or proliferative diabetic retinopathy, such as macular edema or macular ischemia), retinopathy of prematurity (e.g., associated with abnormal growth of blood vessels in the vascular bed supporting the developing retina), venous occlusive disease (e.g., a retinal vein occlusion, branch retinal vein occlusion or central retinal vein occlusion), arterial occlusive disease (e.g., branch retinal artery occlusion (BRAO), central retinal artery occlusion or ocular ischemic syndrome), central serous chorioretinopathy (CSC), cystoid macular edema (CME) (e.g., affecting the central retina or macula, or after cataract surgery), retinal telangiectasia (e.g., characterized by dilation and tortuosity of retinal vessels and formation of multiple aneurysms, idiopathic JXT, Leber's miliary aneurysms, or Coats' disease), arterial macroaneurysm, retinal angiomatosis, radiation-induced retinopathy (RIRP), or rubeosis iridis (e.g., associated with the formation of neovascular glaucoma, diabetic retinopathy, central retinal vein occlusion, ocular ischemic syndrome, or chronic retinal detachment); distortions and/or blind spots (scotoma); changes in dark adaptation (diagnostic of rod cell health); changes in color interpretation (diagnostic of cone cell health); decrease in visual acuity; cataract (e.g., age-related cataract).

Methods and devices are also described for ophthalmic artery interventional procedures, such as stenting, angioplasty, and atherectomy, performed through a transcervical or transfemoral approach into the ophthalmic artery, either using an open surgical technique or using a percutaneous technique, such as a modified Seldinger technique. Some of these methods and devices are particularly useful in procedures which use reverse or retrograde flow protocols.

These disclosed methods and devices include arterial access sheaths, closure devices, and interventional catheters. These methods and devices are useful for procedures utilizing any method of embolic protection, including distal filters, flow occlusion, retrograde flow, or combinations of these methods, or for procedures which do not use any method of embolic protection. Specific methods and devices for embolic protection are also described.

In particular, methods and devices are disclosed for enabling retrograde or reverse flow blood circulation in the ophthalmic artery in order to limit or prevent the release of emboli into the eye, and/or to employ various procedures for establishing, restoring, or increasing blood flow to the eye.

The present invention also includes a method for treating an ophthalmic artery, comprising: forming a penetration in a wall of a carotid artery; positioning an arterial access sheath through the penetration; causing retrograde blood flow from the ophthalmic artery into the sheath. In some embodiments, the method may also include inserting a delivery catheter through the sheath into a treatment site comprised of the internal carotid artery, the ostium, the junction between the ICA and the OA, the portion of the OA near the ICA, and/or the ophthalmic artery. In this aspect, causing retrograde flow may comprise connecting the arterial access sheath to a passive flow reversal circuit, or it may comprise connecting the arterial access sheath to an active aspiration source such as a syringe or suction pump.

DETAILED DESCRIPTION OF THE INVENTION

Figure 1:
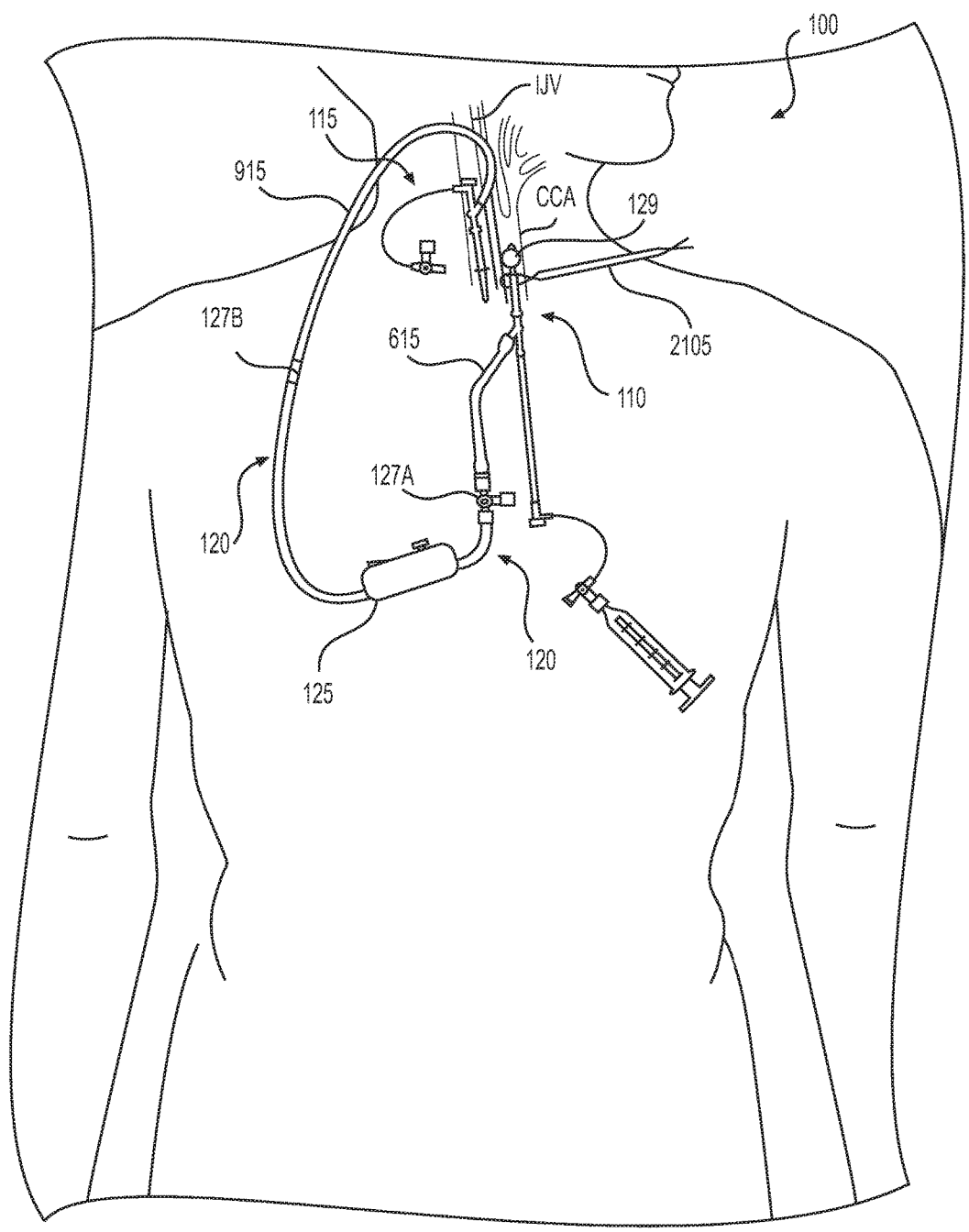
FIG. 1 is an exemplary illustration of a system of devices for transcervical ophthalmic artery procedures using a retrograde blood flow embolic protection system, wherein an arterial access device accesses the ophthalmic artery via a transcervical approach and a venous return device communicates with the internal jugular vein.

The present invention is an apparatus, system, and method of treatment of eye disease using any apparatus or system that involves reverse blood flow or retrograde blood flow. Preferred embodiments of the apparatus, system, and methods induce reverse blood flow or retrograde blood flow in one or more arteries, including but not limited to the ophthalmic artery (OA).

As used herein, reverse flow or retrograde flow refers to the consequences of blocking blood flow in an artery and establishing a fluid flow connection with a vein. Under these conditions, the natural pressure gradient differential causes blood to flow in a reverse direction in the artery. For example, when flow through the internal carotid artery is blocked, the natural pressure gradient between the internal carotid artery and the venous system causes blood to flow in a retrograde or reverse direction from the vasculature of the eye, through the OA, and through the internal carotid artery.

In some embodiments of the invention, retrograde blood flow may be established between an artery and a vein. In preferred embodiments, a reverse flow or retrograde system may be established in any location suitable for treatment of eye disease. These locations include but are not limited to the internal carotid artery, the external carotid artery, the common carotid artery, the supraorbital artery, the supratrochlear artery, the ophthalmic artery; and an appropriate site in the venous system, including but not limited to the internal jugular vein or the femoral vein.

In some embodiments of the invention, retrograde flow is used in combination with other medical procedures and devices to access, treat, and/or deploy a medical device in the fluid flow path between the ICA and the eye. As used herein, fluid flow path refers to a section of the ICA, the ostium, the OA, and other arteries that supply blood to the eye.

A reverse flow system may be variously configured and include a wide number of elements and devices. The typical reverse flow system includes an access device or port into an artery, an access device or port into a vein, one or more tubes or conduits connecting the two access ports, and an occlusion device (e.g., balloon or clamp or the like).

Exemplary reverse and/or retrograde blood flow devices and systems include, but are not limited to U.S. Pat. Nos. 9,259,215; 9,241,699; 9,265,512; 8,545,432; 7,927,347; 7,235,095; 6,936,060; 6,929,634; 6,908,474; 6,905,490; 6,902,540; 6,855,162; 6,827,726; 6,824,558; 6,645,222; 6,641,573; 6,540,712; 6,423,032; 6,413,235; 6,344,054;

6,336,933; 6,302,908; 5,820,595; 5,709,701; and US. Patent applications 20090024072; 20110160762; all of which are incorporated by reference in their entirety.

None of these patents and applications teach the use of reverse flow to treat eye diseases or conditions, or to access the ophthalmic artery.

In accordance with an embodiment of the present invention, eye disease may be treated using at least one arterial access device and a retrograde flow system, using a percutaneous transfemoral approach; a transcervical approach; cervical access; or combinations thereof. The preferred embodiments of the invention use a femoral or cervical approach.

In order to reverse blood flow in the Common Carotid Artery (CCA) during interventional procedures, creation of a circuit is necessary to extract blood from the CCA and return it to a venous location. Extracting blood from the CCA and returning it to a venous location takes advantage of compensatory blood flow through the circle of Willis, high pressure of the arterial system and low pressure of the venous system. Reversing blood flow allows for filtration of the blood so that particulates generated during an interventional procedure are removed from circulation thereby preventing/reducing the possibility of an embolic event. Several structures are typically required to create the reverse blood flow circuit: 1) an Artery Sheath which provides access to the artery; 2) an arterial occlusion device, typically catheter based, which is inserted into the artery via the sheath. This device will incorporate a distal inflatable element, typically similar in design to an angioplasty balloon, which is designed to be positioned into the artery and inflated. The balloon is dimensionally designed to occlude the artery such that normal antegrade blood flow will be stopped upon full inflation and forced through one of the device lumens during the reverse flow portion of the procedure. This device will have one or more thru lumens capable of carrying blood and inserting medical instruments as well as a port (stopcock) for accessing these lumens and connecting to a venous entry for returning the blood. 3) A Venous Sheath. This sheath provides access to the venous system and may include a port (stopcock) for connecting to the circuit to serve as the return point for the arterial blood. 4) A blood filter. This filter is designed with micropores that filter out particulate, but allow blood to flow from one side to the other. This filter may have lure connecters on each end to allow for connection to the reverse flow circuit. 5) IV lines. These lines connect the occlusion device port (stopcock) to the filter and the filter to the venous sheath port (stopcock).

One or more methods of the present invention include but are not limited to inserting and/or delivering an arterial access device to a desired artery and position, blocking flow in the artery, and allowing retrograde or reverse flow to cause blood to flow in a reverse or retrograde flow direction and into a shunt. The retrograde blood flow may then be directed through the venous return device into a vein.

Some embodiments of the invention include high flow capacity, one aspect of which may be a delivery apparatus having a large bore. Having a large bore also may include a large internal dimension, useful for example, in delivering and using certain transcatheter devices.

One skilled in the art will recognize that lumen size for the system (circuit) components (include catheters, sheaths, stopcocks and filters) may be optimized for a particular location and/or circuit. Average CCA diameters can be in the 6.0 mm/18 Fr (or larger) range and average IJV diameters can be in the 13 mm/>Fr 34 (or larger) range. Larger than 2.66 mm/Fr 8 to accommodate these artery/vein sizes may also be used.

One skilled in the art will recognize that pore size of one or more filters may be optimized and/or coordinated in order to achieve medically appropriate filtration. In accordance with some embodiments of the invention, the system may include one or more filters; in systems having more than one filter, the pore size of the filters may be the same or different.

According to some embodiments of the invention, the circuit may be optimized for length. The inventors believe that carotid access may be beneficial, in part because of a circuit in which the guidewire may be approximately 15 inches in length.

In some embodiments of the invention, the reverse flow system is used to access or treat an arterial area or segment between the ICA and the eye. Such treatment includes but is not limited to removing a blockage. In some embodiments, treatment includes restoring or increasing blood flow to the eye. In preferred embodiments, the treatment, apparatus, or system removes a blockage or constriction in the OA near the ICA, e.g., in the ostium and/or in the first section of the OA before the sharp bend in the artery.

Restoring and/or increasing blood flow is used herein to refer to any device, method, therapy, or combination that changes the blood flow to the eye. Examples of such include, but are not limited to increasing the blood flow anywhere in the vasculature leading to the eye or a portion of the eye; removing or opening an obstruction in the fluid flow path in the vasculature leading to the eye, e.g., from the ICA through the OA; delivering and deploying a stent in the fluid flow path in the vasculature leading to the eye; using atherectomy or similar devices to physically remove portions of any obstructions in the vasculature leading to the eye or portion of the eye; and localized drug and/or an oxygen device for increasing flow or amount of oxygen in one or more eye tissues. In some an embodiments, a device or method of the present invention may be combined with a known or new drug or oxygen device in order to treat one or more eye diseases or conditions.

The present invention may also include restoring and/or increasing the amount of nutrients that is available to one or more parts of the eye or to the eye area, specifically by removing or partially opening a blockage in one or more of the arteries that supplies blood flow to the eye. In preferred embodiments of the invention, a blockage is removed or opened in the Internal Carotid Artery, the Ophthalmic Artery, the ostium (as used herein, referring to the junction between the ICA and the OA), or combinations thereof. To or near the eye, as used herein, refers to the vasculature system that supplies blood to the various structures of the eye. As noted above, nutrients as used herein includes but is not limited to oxygen, hemoglobin, complement, and glucose.

The present invention may also include methods, devices, and systems for removing a blockage in the ostium or a proximal segment of the OA near the ICA. In these embodiments, removing the blockage comprises opening a channel or access through the ostium sufficient to provide a therapeutically beneficial result to the eye, the rear of the eye, or portions thereof. The present invention also includes restoring and/or improving blood flow anywhere in the vascular pathway to or within the eye.

Therapeutically beneficial result is used herein to refer to any perceived or actual benefit to the patient. Examples of beneficial results include but are not limited to: treatment of an eye disease, condition, and/or symptom; restoring or increasing blood flow in any manner that treats an eye disease, condition, and/or symptom; and removing or partially removing a blockage in the blood flow path between the heart and the eye, preferably in the ophthalmic artery or a portion thereof.

Applicants and inventors intend that the invention should not be limited solely to changing vascular flow in order to improve or restore the amount of nutrients that are delivered to the eye. For example, in some embodiments of the invention, the vascular flow may be unaffected for the most part, but the amount or concentration of nutrients may be increased, thereby increasing the amount of nutrients that may be delivered to the eye or associated with the eye. One skilled in the art may recognize, with the teaching of this invention, that there are other biological systems or capabilities that may be used to increase the amount of nutrients that are delivered to the eye.

In this and other embodiments of the invention, reducing blockage includes but is not limited to piercing or penetrating the blockage. In most preferred embodiments of the invention, piercing and penetrating the blockage refers to obtaining sufficient blood and/or fluid flow through or around the blocked vascular area sufficient to provide a therapeutically beneficial amount of oxygen to the eye or a portion of the eye.

Some embodiments of the present invention include a retrograde flow system that does not require the use of a balloon or the like. In these balloonless systems, methods, and assemblies the flow direction element may be an external force applied to an artery to compress the artery around the sheath. As used herein, external force refers to any element or structure that functions to apply force, to clamp or close the artery against the sheath. Exemplary elements include, but are not limited to, a clamp, vise, band, suture, pincer, contractor, constrictor, and the like. In function, any such element compresses or closes the artery against the sheath or tube, thereby forcing any blood flow through the lumen of the tube rather than around the tube.

An embodiment of the inventions includes methods and devices for treating a non-human animal. Some embodiments of the invention include treating a dog, including but not limited to treating central serous retinopathy.

In accordance with the present invention, a reverse flow system may be variously configured and include a variety of elements and components. Typical components and elements include, but are not limited to: an arterial access device; a venous return device; one or more shunts; a flow control assembly; an arterial port; a venous port; a shunt valve; a flush line; one or more shut off valves; one or more connectors; one or more tubing members; one or more syringes; one or more vessel closure devices; one or more suture delivery devices; one or more interventional catheters; one or more interventional delivery devices; one or more external receptacles; one or more adapters; one or more Y connectors; a flow state indicator; a flow rate activator, one or more sensors; a timer; contrast; one or more stopcocks; one or more manifolds.

The invention may also include a delivery system configured or adapted to position and/or orient a medical device in the OA; atherectomy or angioplasty in the OA; all in combination with a reverse flow system.

The retrograde flow system 100 can include the arterial access device 110, venous return device 115, and shunt 120 which provides a passageway for retrograde flow from the arterial access device 110 to the venous return device 115. The system also may include the flow control assembly 125, which interacts with the shunt 120 to regulate and/or monitor retrograde blood flow through the shunt 120. Embodiments of the components of the retrograde flow system 100 are described below.

FIG. 1 shows an exemplary embodiment of a retrograde flow system 100 that is adapted to establish and facilitate retrograde or reverse flow blood circulation in the ophthalmic artery in order to limit or prevent the release of emboli into the eye. The system 100 interacts with the ophthalmic artery to provide retrograde flow from the vasculature of the eye to a venous return site, such as the internal jugular vein (or to another return site such as another large vein or an external receptacle in alternate embodiments.) The retrograde flow system 100 can include an arterial access device 110, a venous return device 115, and a shunt 120 that provides a passageway for retrograde flow from the arterial access device 110 to the venous return device 115.

An optional flow control assembly 125 can interact with the shunt 120. The flow control assembly 125 can be adapted to regulate and/or monitor the retrograde flow from the ophthalmic artery to the internal jugular vein. Optionally, the flow control assembly can be replaced with or used in conjunction with an in-line filter. The flow control assembly 125 can interact with the flow pathway through the shunt 120, either external to the flow path, inside the flow path, or both.

The illustrated embodiment shows occluding the CCA. In preferred embodiments the occlusion element is positioned in and occludes the ICA and/or the OA.

The arterial access device 110 can at least partially insert into the internal carotid artery (ICA) and/or the ophthalmic artery (OA) and the venous return device 115 at least partially inserts into a venous return site such as the internal jugular vein (IJV). The arterial access device 110 and the venous return device 115 couple to the shunt 120 at connection locations 127a and 127b. When flow through the ICA is blocked, the natural pressure gradient between the internal carotid artery and the venous system can cause blood to flow in a retrograde or reverse direction from the eye vasculature through the ophthalmic artery and the internal carotid artery, and through the shunt 120 into the venous system. The flow control assembly 125 can modulate, augment, assist, monitor, and/or otherwise regulate the retrograde blood flow.

In an alternative embodiment, the flow control assembly may be replaced with an inline blood filter; or the flow control assembly may be used in combination with an inline blood filter.

In the embodiment of FIG. 1, the arterial access device 110 can access the common ophthalmic artery CCA via a transcervical approach. Transcervical access provides a short length and non-tortuous pathway from the vascular access point to the target treatment site thereby easing the time and difficulty of the procedure, compared for example to a transfemoral approach. Additionally, this access route reduces the risk of emboli generation from navigation of diseased, angulated, or tortuous ICA or OA anatomy. At least a portion of the venous return device 115 can be placed in the internal jugular vein IJV. In an embodiment, transcervical access to the ophthalmic artery is achieved percutaneously via an incision or puncture in the skin through which the arterial access device 110 is inserted. An occlusion element 129, such as an expandable balloon, can be used to occlude the ICA or OA at a location proximal of the distal end of the arterial access device 110. The occlusion element 129 can be located on the arterial access device 110 or it can be located on a separate device. In an alternate embodiment, the arterial access device 110 accesses the ICA and the OA via a direct surgical transcervical approach. In the surgical approach, the ophthalmic artery can be occluded using a tourniquet 2105. The tourniquet 2105 is shown in phantom to indicate that it is a device that is used in the optional surgical approach.

Some embodiments of the present invention include an arterial access device adapted and configured for use only with an interventional reverse flow system. In these embodiments, there is no need for a vascular surgeon or cut-down procedure. In devices, methods, and systems according to this embodiment, a neuroradiologist or interventionalist is the only type of physician required to perform the procedure.

Figure 2:
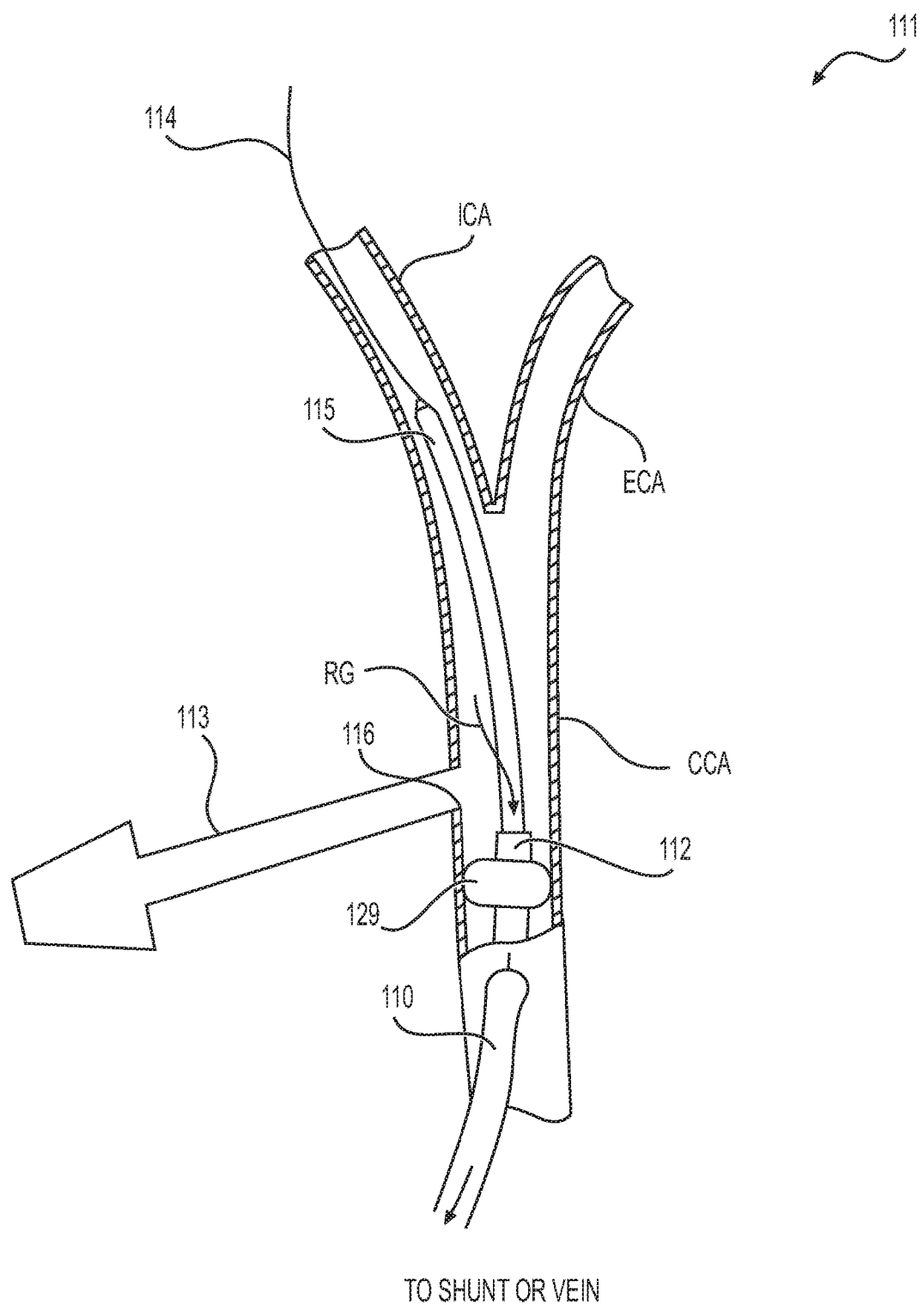
FIG. 2 shows an embodiment of an arterial access device.

In this embodiment, an example of which is shown in FIG. 2, the arterial access device or system 111 includes a device delivery system 115, which may include an occlusion element 129, such as a balloon or expandable member, to block the blood flow; a conduit 112 or catheter having a lumen through which retrograde blood may pass (RG); and a guidewire 114. The access device or system 111 also includes a sheath 113 having a distal end 116 configured to be flush with the internal wall of the artery and located in a position near but above the occlusion element 129.

In the illustrated embodiment, the sheath accesses the artery through a skin puncture in the neck (not a surgical cut-down), and the catheter accesses the artery through a cut-down procedure. In preferred embodiments of the invention, the sheath accesses the artery through a skin stick in the neck and the interventional catheter accesses the artery through a femoral access in the groin.

For any of the embodiments of the arterial access device, the sheath is adapted to be introduced through an incision or puncture in a wall of a common carotid artery, either an open surgical incision or a percutaneous puncture established, for example, using the Seldinger technique. The length of the sheath can be in the range from 5 to 15 cm, usually being from 10 cm to 12 cm. The inner diameter can be in the range from 7 Fr (1 Fr=0.33 mm) to 10 Fr, usually being 8 Fr.

The illustrated embodiment shows reverse flow through the catheter. Alternatively, reverse blood flow may pass through the sheath. In preferred embodiments of the invention, reverse flow can occur through either the sheath or the catheter, and procedure devices can pass through whichever of the sheath or catheter that is not being used for reverse flow.

This configuration provides many advantages and alternatives. Reverse flow can pass through the conduit, the sheath, or both. The conduit may be connected to a shunt, receptacle bag, or vein (e.g., IJV or femoral vein). The catheter comprising conduit 112 may be used without impinging the function of the sheath, and vice-versa. As noted above, a vascular surgeon is not required. Also this access device configuration is suitable for use with a cervical (carotid) or femoral access. In a preferred embodiment, access is cervical, primarily because such a location saves approximately ten minutes procedure time over femoral access, thus reducing the patient time in surgery and decreasing the amount of time the patient is subject to stroke risk.

The arterial access device can have various features particularly useful in a retrograde blood flow system. As shown in FIG. 1, the arterial access device 110 can include a flow lines 615 and 915 and a Y-adaptor to connect the sheath to a retrograde flow system. Optionally, the distal sheath may include an occlusion element 129 for occluding flow through, for example the common carotid artery. If the occluding element 129 is an inflatable structure such as a balloon or the like, the sheath can include an inflation lumen that communicates with the occlusion element 129. The occlusion element 129 can be an inflatable balloon, but it can also be an inflatable cuff, a conical or other circumferential element which flares outwardly to engage the interior wall of the carotid artery to block flow, a membrane-covered braid, a slotted tube that radially enlarges when axially compressed, or similar structure which can be deployed by mechanical means, or the like. In the case of balloon occlusion, the balloon can be compliant, non-compliant, and elastomeric; reinforced; or have a variety of other characteristics. In an embodiment, the balloon is an elastomeric balloon which is closely received over the exterior of the distal end of the sheath prior to inflation. When inflated, the elastomeric balloon can expand and conform to the inner wall of the carotid artery. In an embodiment, the elastomeric balloon is able to expand to a diameter at least twice that of the non-deployed configuration, frequently being able to be deployed to a diameter at least three times that of the un-deployed configuration, more preferably being at least four times that of the un-deployed configuration, or larger.

In some embodiments of the invention, the arterial access device may include a catheter having a backstop; a balloon, typically attached to a central guidewire; and a knot or the like (some other geometrically shaped element) extending on the guidewire outwardly and distally from the balloon. In use, the knot may be deployed in the region of the plaque or obstruction; the knot may be used to loosen particles in the artery, which flow back toward backstop and/or catheter. The balloon may then be partially deployed, whereby particles may become trapped between the balloon and the end of the catheter (or backstop). The balloon may then be drawn back into the catheter, thereby drawing and capturing particles within the lumen of the catheter. The catheter, carrying the particles, may then be pulled out of the body.

Alternative elements or structures of the system described in the invention may include a guidewire with a distal tip comprising a kite tail shaped element; a backstop comprising a funnel shaped cage; a balloon that is deployed and/or expanded in stages, e.g., the proximal end first, thereby forcing, pushing, or capturing particles into the backstop.

The system 100 is adapted to regulate retrograde flow in a variety of manners. Any combination of the pump, valve, syringe, and/or variable resistance component can be manually controlled by the user or automatically controlled via a controller to adjust the retrograde flow rate. Thus, the system 100 can regulate retrograde flow in various manners, including controlling an active flow component (e.g., pump, syringe, etc.), reducing the flow restriction, switching to an aspiration source (such as a pre-set VACULOK syringe, VACUTAINER, suction system, or the like), or any combination thereof Methods of Use Initially, the distal sheath of the arterial access device 110 is introduced into a carotid artery and into the internal carotid artery. As noted above, entry into the carotid artery can be via a transcervical or transfemoral approach, or any approach suitable for introducing a distal portion of a catheter into the ophthalmic artery. After the sheath of the arterial access device 110 has been introduced into the internal carotid artery, the blood flow will continue in antegrade direction with flow from the ophthalmic artery entering both the internal carotid artery ICA and the external carotid artery ECA.

The venous return device 115 can then be inserted into a venous return site, such as the internal jugular vein IJV. The shunt 120 can be used to connect the flow lines 615 and 915 of the arterial access device 110 and the venous return device 115, respectively (as shown in FIG. 1). In this manner, the shunt 120 provides a passageway for retrograde flow from the atrial access device 110 to the venous return device 115. In another embodiment, the shunt 120 can connect to an external receptacle rather than to the venous return device 115.

Once all components of the system are in place and connected, flow through a carotid artery, ICA, or OA can be stopped, such as using the occlusion element 129 as shown in FIG. 1. The occlusion element 129 can be expanded at a location proximal to the distal opening of the sheath to occlude the OA. Alternately, the tourniquet 2105 or other external vessel occlusion device can be used to occlude the ophthalmic artery to stop flow. In an alternative embodiment, the occlusion element 129 can be introduced on second occlusion device 112 separate from the distal sheath 605 of the arterial access device 110. The OA can also be occluded with a separate occlusion element, either on the same device 110 or on a separate occlusion device.

At that point retrograde flow from the OA and internal carotid artery ICA can begin and can flow through the sheath, the flow line 615, the shunt 120, and into the venous return device 115 via the flow line 915. The flow control assembly 125 can regulate the retrograde flow as described above. While the retrograde flow is maintained, a stent delivery catheter can be introduced into the sheath. The delivery catheter can be introduced into the sheath through a hemostasis valve and the proximal extension of the arterial access device 110. The delivery catheter can be advanced into the internal carotid artery ICA and the OA.

Vibrating Guidewire

Some embodiments of the present invention may include a conventional guidewire; some embodiments of the invention include a guidewire with a basket or the like on the distal end; other embodiments of the invention may include a guidewire having a geometrically shaped element on the distal end.

This guidewire is intended for neuro interventional procedures in which a reverse flow system is in use. The guidewire is designed to be used in cervical access where there is need to remove plaque from a specific arterial segment. Once reverse flow is established, the guidewire is placed in the location of the stenosis and a vibration is induced via an electric motor. This vibration may loosen material either due to direct contact with general vibration, or with contact and by use of a specific resonance frequency of the target material for removal. The guidewire is of general design, however it is optimized for cervical access procedures and is designed to fit within the vibratory motor housing in such a way as to contact the motor. Contact with this motor imparts a vibration in the guidewire which is transmitted to the target anatomy and serves to aid in the removal of plaque.

In preferred embodiments of the invention the vibratory motor is positioned on and or attached to a surgical drape. It is intended that the vibratory motor should remain substantially stationary. The guidewire passes through or is attached to the vibratory motor. Positioning in the target anatomy is accomplished by moving the guidewire in and out of the arterial segment being treated.

Vibrating Angioplasty Balloon

A balloon according to these embodiments of the invention may be a conventional balloon or may include geometric features intended to facilitate plaque/obstruction removal or dislodgement. Balloons may be of any of a variety of shapes (asymmetrical, spiral, etc.) and/or coated with materials for facilitating plaque removal (abrasives, etc.).

This balloon is intended for neuro interventional procedures in which a reverse flow system is in use. The balloon is designed to be used in cervical access where there is need to remove plaque from a specific arterial segment. Once reverse flow is established, the balloon is placed in the location of the stenosis and a vibration is induced via an electric motor. This vibration may loosen material either due to direct contact with general vibration, or with contact and by use of a specific resonance frequency of the target material for removal. The balloon is of general design, however it is optimized for cervical access procedures and is designed to fit within the vibratory motor housing in such a way as to contact the motor. Contact with this motor imparts a vibration in the balloon which is transmitted to the target anatomy and serves to aid in the removal of plaque.

In accordance with the present invention, the vibratory balloon, and/or the vibratory guidewire may loosen plaque or an obstruction, and plaque/obstruction particles and the like may be removed from the site using the reverse flow system.

In another embodiment, a medical device or agent is capable of delivering drugs to the ostium for the purpose of improving vascular blood flow at the ostium and within the OA. These drugs may include (but are not limited to) low dose Viagra (or equivalent PDE 5 inhibitor), Lucentis, Avastin, Taxol, Rapamyacin or other pharmaceuticals used to improve vascular blood flow.

Embodiments of the present invention and the various components or elements thereof can be used interchangeably so that features and functions of one exemplary embodiment of a filter device can be used with other embodiments of the filter device. Additionally, methods of using one embodiment of the present invention can be used with other embodiments of the present invention.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

EXAMPLES

Example 1

The inventors believe that compromised blood flow to the vasculature of the posterior eye directly contributes to diseases of the eye. This lack of normal blood flow may originate in the internal carotid artery (ICA), the ophthalmic artery (OA), branches of the ophthalmic artery, have a cardiac origin, and/or combinations thereof, and be directly caused by a blockage in one or more of these vessels. This lack of sufficient blood flow directly contributes to inadequate nutrient levels seen in tissues such as the choroid, retina, optic nerve and other ophthalmic anatomy. This blockage may manifest as stenosis, lesions or other physiology within the ophthalmic related vasculature and compromise normal blood flow such that the posterior eye vasculature does not receive an adequate nutrient supply for maintenance of normal function. As a result it is possible for a cascade of events to initiate which may result in various diseases of the eye.

Linear and volumetric blood flow was measured for healthy controls and diseased patients (with confirmed AMD diagnosis). Flow rates were measured for the Left Ophthalmic Artery (LOA), Right Ophthalmic Artery (ROA), Left Internal Carotid Artery (LICA) and Right Internal Carotid Artery (RICA) using Phased Contrast Magnetic Resonance Imaging (PCMRI) technique on a 7 Tesla Nmri machine. These flow rates were measured in cm/sec for linear flow and in ml/min for volumetric flow. The average diameter of the ICA for a healthy control is 46 mm and the average diameter of the OA for a healthy control is 12 mm. Average values for the same vessels in diseased patients were 4.18 mm for the ICA and 0.86 mm for the OA.

Specific linear and volumetric flow rates were compared, and the OA flow data shows a medically or clinically observable difference between the flow rates for healthy controls compared to diseased patients. Specific flow rates were compared, and the ICA flow data shows a medically or clinically observable difference between the flow rates for healthy controls compared to diseased patients. In every case, the blood flow rate for the diseased patients appears to be lower than the blood flow rate for the healthy controls.

Example 2

In a cadaveric tissue, we removed the right ICA and visually examined the ostium. We confirmed blockage of the OA at the ostium (which appeared to be complete). Once the section of left ICA was removed, we were able to gain internal access to the OA ostium and insert a micro PTCA balloon catheter. We performed this test to visually observe the effect of placing and inflating a balloon catheter in the OA. This (non-compliant) balloon catheter has a maximum diameter of 0.85 mm at 16 atms, with a crossing profile of 0.74 mm and a working length of approximately 5 mm. We inflated the balloon several times to approximately 12 atms max and observed the balloon through the vessel. The vessel appeared to tolerate the inflations without obvious damage.

Example 3

A system of the present invention is designed to induce reverse blood flow in the cerebral vasculature during neuro interventional procedures. This system provides protection from particulate related stroke during these procedures. Enhancements to the basic system include:

Common carotid artery to internal jugular vein circuit. This pathway reduces the overall device length required to reach the target anatomy. While this procedure requires cervical access, there is no need to do femoral access and expose the patient to the potential issues related to crossing the arch. This type of connection between an artery and vein is commonly referred to as a fistula.

Addition of an in line filter to capture particulate.

Sizing the tubing, stock cocks and filter such that a minimal resistance to flow is encountered by blood as it travels through the device. It is anticipated the device will be 8.5 to 9.0 French. Maximizing the internal diameter of the various components allows for blood to flow at the most rapid velocity.

Addition of a circuit to connect the CCA flow to the supra orbital artery. This connection will provide flow directly to the OA so that flow is reversed. This OA reverse flow will prevent embolization of the OA/central retinal artery during interventional procedures.

Specially designed CCA occlusion balloon designed to reduce probability of low or no flow zones in the CCA.

Example 4

In some embodiments of the invention, this flow direction element of the system is used to initiate the reversal of flow in the Common Carotid Artery (CCA). Typically, CCA flow reversal may be accomplished by use of an inflatable balloon device. CCA flow reversal may also be accomplished without the need for a balloon by using a sheath that has external force applied to compress the CCA against the tube portion of the sheath. This compressive action serves to prevent blood flow around the sheath (in the same way as an inflatable balloon does from inside the CCA) and force blood through the sheath and into the venous circuit of the system, thereby providing flow reversal. The sheath may be of conventional design, or may contain elements that facilitate compressing the CCA against the sheath for the purpose of establishing flow reversal.

Methodology and Purpose of Examples 5 and 6:

1) Dissection of specimens diagnosed with AMD for the purpose of identifying CAD disease (plaque) in the carotid siphon/ophthalmic ostium and to provide evidence of the ability to cannulate and deliver an angioplasty balloon to the ophthalmic artery ostium.

2) Dissection of a specimen (with cervical segment) diagnosed with AMD to identify CAD disease (plaque) in the carotid siphon/ophthalmic ostium.

Terminology: OA—Ophthalmic artery; LOA—Left ophthalmic artery; ROA—Right Ophthalmic artery; ICA—Internal carotid artery; LICA—Left internal carotid artery; RICA—Right internal carotid artery; CCA—Common carotid artery; LCCA—Left common carotid artery; RCCA—Right common carotid artery; Cow—Circle of Willis A true endovascular approach requires an imaging modality that relies on injection of contrast, which is not possible in static tissue samples such as a cadaver. Based on these limitations, the following two Examples show balloon placement and inflation directly in the exposed ophthalmic ostium in situ and post dissection.

Example 5

The primary goal for dissection of a specimen with bilateral AMD was to prove that it is possible to place and dilate an angioplasty balloon catheter in the segment of the OA just distal to the ICA ostium, prior to the typical OA 90° bend, without dissecting the OA.

We used an angioplasty balloon that has a maximum inflated diameter of 0.8 mm at 16 ATMs, and a working length of approximately 3.5 mms.

We identified the left and right internal carotid artery (ICA)/Ophthalmic Artery (OA) ostiums in the first specimen and removed material from the sphenoid to expose the ophthalmic artery (OA). We positioned the balloon catheter into the left OA (LOA) and inserted the balloon such that the working length of the balloon did not extend beyond the desired segment of the LOA.

The balloon was able to be delivered and inflated at the desired location of the LOA, within the ostium of the LOA.

We then examined both ostiums for evidence of plaque in the ICA, OA, and ostium in situ. We identified plaque formation at the ostium of the transected LICA, and plaque formation in the walls of the LICA. Likewise, we also identified plague formation in the RICA, at the ostium of the transected ROA and in the walls of the RICA.

We were able to successfully position and inflate an angioplasty balloon within the target LOA anatomy. We were also able to identify plaque formation in both the LICA and RICA as well as both the ROA and LOA ostium.

Example 6

The primary goal for dissection of this specimen was to prove that it is possible to place and dilate an angioplasty balloon catheter in the segment of the OA just distal to the ICA ostium, prior to the typical OA 90° bend, without dissecting the OA. The secondary goal was to examine each ICA/OA ostium for evidence of plaque. We identified the left and right ICA/OA ostiums without having to remove material from the sphenoid and could visualize plaque in both ICA segments in situ. In addition, we could clearly see plaque formation in the LOA.

We removed both the left and right ICA vessel segments and transected each. In both samples, we observed blockage directly at the ophthalmic ostium.

We examined both the inside and outside of the LICA vessel. We could clearly see a plaque formation at the base of OA near the ostium. We dissected the LOA from the LICA at the ostium to expose the plaque. The plaque formation was clearly seen in the ostium of the LOA.

We used the RICA vessel segment to place the balloon catheter. The balloon catheter was positioned into the ROA and inserted such that the working length of the balloon did not extend beyond the desired segment of the ROA (as noted in the previous Example).

We were able to successfully position and inflate an angioplasty balloon within the target ROA anatomy. We were also able to identify plaque in both the LICA and RICA as well as both the ROA and LOA ostium. This plaque appeared to be blocking or nearly blocking the OA in both the left and right ostiums.

We claim:

1. A method, comprising:
    inducing retrograde flow in an artery to establish induced retrograde flow and to stop antegrade flow in an ophthalmic artery of a subject;
    positioning a first device within the ophthalmic artery;
    treating at least one of the ophthalmic artery or a junction between an internal carotid artery and the ophthalmic artery of the subject, with the first device; and
    delivering the induced retrograde flow to the venous system of the subject.

2. The method of claim 1, wherein inducing retrograde flow in the artery includes intravascularly inducing retrograde flow in the artery.

3. The method of claim 1, wherein inducing retrograde flow in the artery causes retrograde flow in the ophthalmic artery.

4. The method of claim 1, further including:
    restoring antegrade blood flow in the ophthalmic artery.

5. The method of claim 1, further including:
    increasing nutrient delivery to the ophthalmic artery.

6. The method of claim 1, wherein positioning the first device within the ophthalmic artery of a subject includes extending the first device through a lumen of another device located within an arterial system of the subject.

7. A method, comprising:
    intravascularly introducing a first device into a subject, the subject having an ophthalmic artery with a first antegrade blood flow rate therein;
    inducing retrograde blood flow in a carotid artery;
    positioning the first device within the ophthalmic artery;
    without the first antegrade blood flow in the ophthalmic artery, treating tissue of the ophthalmic artery or a junction of an internal carotid artery and the ophthalmic artery, via the first device; and
    after treating tissue, ceasing retrograde blood flow in the carotid artery.

8. The method of claim 7, wherein, after ceasing retrograde blood flow, the ophthalmic artery has a second antegrade blood flow rate greater than the first antegrade blood flow rate.

9. The method of claim 7, further including increasing nutrient delivery to the ophthalmic artery.

10. The method of claim 7, wherein treating tissue of the ophthalmic artery or the junction of the internal carotid artery and the ophthalmic artery includes removing tissue of at least one of a lesion or a blockage.

11. The method of claim 10, wherein the inducing the retrograde blood flow includes inducing retrograde flow distal of the at least one of the lesion or the blockage.

12. The method of claim 7, further including:
    positioning a second device within a venous system of the subject; and
    delivering the induced retrograde blood flow to the venous system via the second device.

13. The method of claim 7, further including filtering the induced retrograde blood flow.

14. A method, comprising:
    inducing retrograde flow in an ophthalmic artery of a subject;
    positioning a first device within the ophthalmic artery of the subject; and
    filtering the induced retrograde flow.

15. The method of claim 14, further including:
    positioning a second device within an internal carotid artery of the subject.

16. The method of claim 15, wherein positioning the first device within the ophthalmic artery of the subject includes delivering the first device through a lumen of the second device.

17. The method of claim 14, further including:
    ceasing the retrograde flow in the ophthalmic artery of the subject.

18. The method of claim 14, further including:
    delivering the filtered induced retrograde flow to a venous system of the subject.

19. The method of claim 14, wherein the inducing retrograde flow in the ophthalmic artery includes occluding an internal carotid artery of the subject.

20. The method of claim 14, further including:
treating tissue of the ophthalmic artery or a junction of an internal carotid artery and the ophthalmic artery, via the first device.

21. A method, comprising:
positioning a first device within an ophthalmic artery of a subject, wherein the ophthalmic artery has a first antegrade blood flow rate;
inducing retrograde blood flow in a carotid artery and the ophthalmic artery;
treating tissue of the ophthalmic artery or a junction of the internal carotid artery and the ophthalmic artery, via the first device; and
ceasing retrograde blood flow in the carotid artery;
wherein after ceasing retrograde blood flow, the ophthalmic artery has a second antegrade blood flow rate greater than the first antegrade blood flow rate.

22. The method of claim 21, wherein treating tissue of the ophthalmic artery or a junction of the internal carotid artery and the ophthalmic artery includes treating tissue of the ophthalmic artery.

23. The method of claim 22, further comprising filtering the retrograde blood flow during the treating tissue step, wherein filtering the retrograde blood flow includes capturing emboli.

24. The method of claim 21, wherein treating tissue of the ophthalmic artery or a junction of the internal carotid artery includes treating at least one of a complete blockage or a partial blockage of an ophthalmic artery via at least one of a stenting, an angioplasty, an atherectomy, or a drug treatment.

25. The method of claim 21, wherein the first antegrade blood flow rate and the second antegrade blood flow rate are volumetric blood flow rates.

26. The method of claim 21, wherein the first antegrade blood flow rate and the second antegrade blood flow rate are linear blood flow rates.

27. The method of claim 21, wherein the second blood flow rate increases an amount of a nutrient to the eye, relative to an amount of the nutrient to the eye from the first blood flow rate, wherein the nutrient includes one or more of oxygen, hemoglobin, complement, and glucose.

28. The method of claim 21, wherein inducing retrograde blood flow in the ophthalmic artery causes blood flow from an artery to a venous system via a connection between the artery and the venous system.

29. The method of claim 28, wherein inducing retrograde blood flow in the ophthalmic artery includes occluding the internal carotid artery.

30. The method of claim 21, further comprising controlling the inducing of retrograde blood flow, via a pump, a syringe, a valve, or an aspiration source.

* * * * *

UNITED STATES PATENT AND TRADEMARK OFFICE
CERTIFICATE OF CORRECTION

PATENT NO. : 10,143,585 B2
APPLICATION NO. : 15/971680
DATED : December 4, 2018
INVENTOR(S) : Michael Calhoun, Jeff Franco and Robert M. Vidlund Page 1 of 1

It is certified that error appears in the above-identified patent and that said Letters Patent is hereby corrected as shown below:

In the Specification

In Column 13, Lines 26-27, "...the ICA for a healthy control is 46 mm and the average diameter of the OA for a healthy control is 12 mm." should be "...the ICA for a healthy control is 4.6 mm and the average diameter of the OA for a healthy control is 1.2 mm."

Signed and Sealed this
Nineteenth Day of February, 2019

Andrei Iancu
*Director of the United States Patent and Trademark Office*